US012515040B2

(12) United States Patent
Dunlap et al.

(10) Patent No.: US 12,515,040 B2
(45) Date of Patent: Jan. 6, 2026

(54) VIRTUAL PATCH ELECTRODES FOR ELECTRICAL STIMULATION

(71) Applicant: Battelle Memorial Institute, Columbus, OH (US)

(72) Inventors: Collin F. Dunlap, Columbus, OH (US); Sam Colachis, Columbus, OH (US); Joshua R. Branch, Columbus, OH (US); Ian Baumgart, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 295 days.

(21) Appl. No.: 18/222,832

(22) Filed: Jul. 17, 2023

(65) Prior Publication Data

US 2023/0355961 A1 Nov. 9, 2023

Related U.S. Application Data

(63) Continuation-in-part of application No. 17/390,282, filed on Jul. 30, 2021, now Pat. No. 11,701,512.

(60) Provisional application No. 63/058,914, filed on Jul. 30, 2020.

(51) Int. Cl.
*A61N 1/04* (2006.01)

(52) U.S. Cl.
CPC ......... *A61N 1/0484* (2013.01); *A61N 1/0452* (2013.01)

(58) Field of Classification Search
CPC .. A61N 1/0484; A61N 1/0452; A61N 1/3603; A61N 1/36003
See application file for complete search history.

(56) References Cited

U.S. PATENT DOCUMENTS

| | | | | |
|---|---|---|---|---|
| 2010/0023070 A1* | 1/2010 | Moffitt | A61N 1/36071 | 607/2 |
| 2015/0142090 A1* | 5/2015 | Duijsens | A61N 1/05 | 607/116 |
| 2019/0269903 A1 | 9/2019 | Fahey | | |
| 2020/0022832 A1 | 1/2020 | Hyde et al. | | |
| 2020/0139112 A1* | 5/2020 | Aharonovitch | A61B 5/389 | |
| 2020/0197688 A1 | 6/2020 | Dernebo et al. | | |

* cited by examiner

*Primary Examiner* — Ankit D Tejani
*Assistant Examiner* — Joshua Brendon Solomon
(74) *Attorney, Agent, or Firm* — Volpe Koenig

(57) ABSTRACT

A system for electrical stimulation may comprise a plurality of electrodes and a processor. The processor may be configured to: define a region of interest (ROI) for electrode activation via a first subset of the plurality of electrodes; and define a second subset of electrodes, wherein each electrode within the second subset of electrodes are positioned away from the ROI such that the average distance between each electrode and the ROI is maximized. The second group of electrodes may be defined via low-discrepancy sequences or an equidistributed sequence. The plurality of electrodes may be part of a wearable garment or an implantable device. The system may be for muscle stimulation or neural simulation.

13 Claims, 18 Drawing Sheets

VIRTUAL PATCH ELECTRODES FOR ELECTRICAL STIMULATION

CROSS REFERENCE TO RELATED APPLICATIONS

This application is a continuation-in-part of U.S. patent application Ser. No. 17/390,282, filed Jul. 30, 2021, which claims the benefit of 63/058,914 filed on Jul. 30, 2020, which are incorporated by reference as if fully set forth.

FIELD OF INVENTION

The present application relates generally to electrical stimulation systems, devices and methods, and more particularly to neural and muscle stimulation calibration systems, devices and methods for accelerating stimulation calibration. Muscle stimulation systems may be a functional electrical stimulation (FES) system, neuromuscular electrical stimulation (NMES) systems, or a transcutaneous electrical nerve stimulation (TENS) system.

BACKGROUND

NMES systems (sometimes also referred to as electrical muscle stimulation) use electrical impulses to induce muscular contractions. NMES comprises delivering electrical pulses via electrodes, through skeletal muscles, to activate a motor response. Muscle fibers in skeletal muscles respond to electrical signals sent through motor neurons. NMES induces a foreign electrical current which overrides the natural motor neuron activity and causes a muscle contraction. This may reanimate muscular movement in paralyzed limbs. NMES may also be used to enhance able limbs. Functional electrical stimulation (FES) is a subset of NMES which focuses on promoting functional movement.

Current NMES and TENS garments, including high-density electrode sleeves, are highly susceptible to inter-session and inter-subject variability in electrode positioning. Garment alignment inconsistencies and anatomical differences between subjects and/or users may affect system calibrations, such as NMES patterns used to evoke movement. If the garment position is shifted, a corresponding shift in active electrodes may be required to compensate for the misalignment. Furthermore, anatomical differences between subjects and/or users may require de novo pattern calibration. Calibration may be achieved through trial and error where an operator manually selects individual electrodes for discrete activation and then iteratively refines the pattern. In most (if not all) situations, the operator must manually move each electrode to the proper location. Not only is this process tedious and inefficient, but the discrete states of electrodes may impose a coarse resolution that make fine adjustments difficult.

SUMMARY

A system for electrical stimulation may comprise a plurality of electrodes and a processor. The processor may be configured to: define a region of interest (ROI) for electrode activation via a first subset of the plurality of electrodes; and define a second subset of electrodes, wherein each electrode within the second subset of electrodes are positioned away from the ROI such that the average distance between each electrode and the ROI is maximized. The second group of electrodes may be defined via low-discrepancy sequences or an equidistributed sequence. The first subset of electrodes and second subset of electrodes may have an equally balanced current. The plurality of electrodes may be part of a wearable garment or an implantable device. The system may be for muscle stimulation or neural simulation. Further, the plurality of electrodes may be places in proximity to the muscle or nerve to be simulated.

The first subset of electrodes may be cathodes and the second subset of electrodes are anodes. The anodes may be limited to a specific region. The processor may be further configured to provide electric muscle simulation via the subset of the plurality of electrodes.

DETAILED DESCRIPTION

Figure 1A:
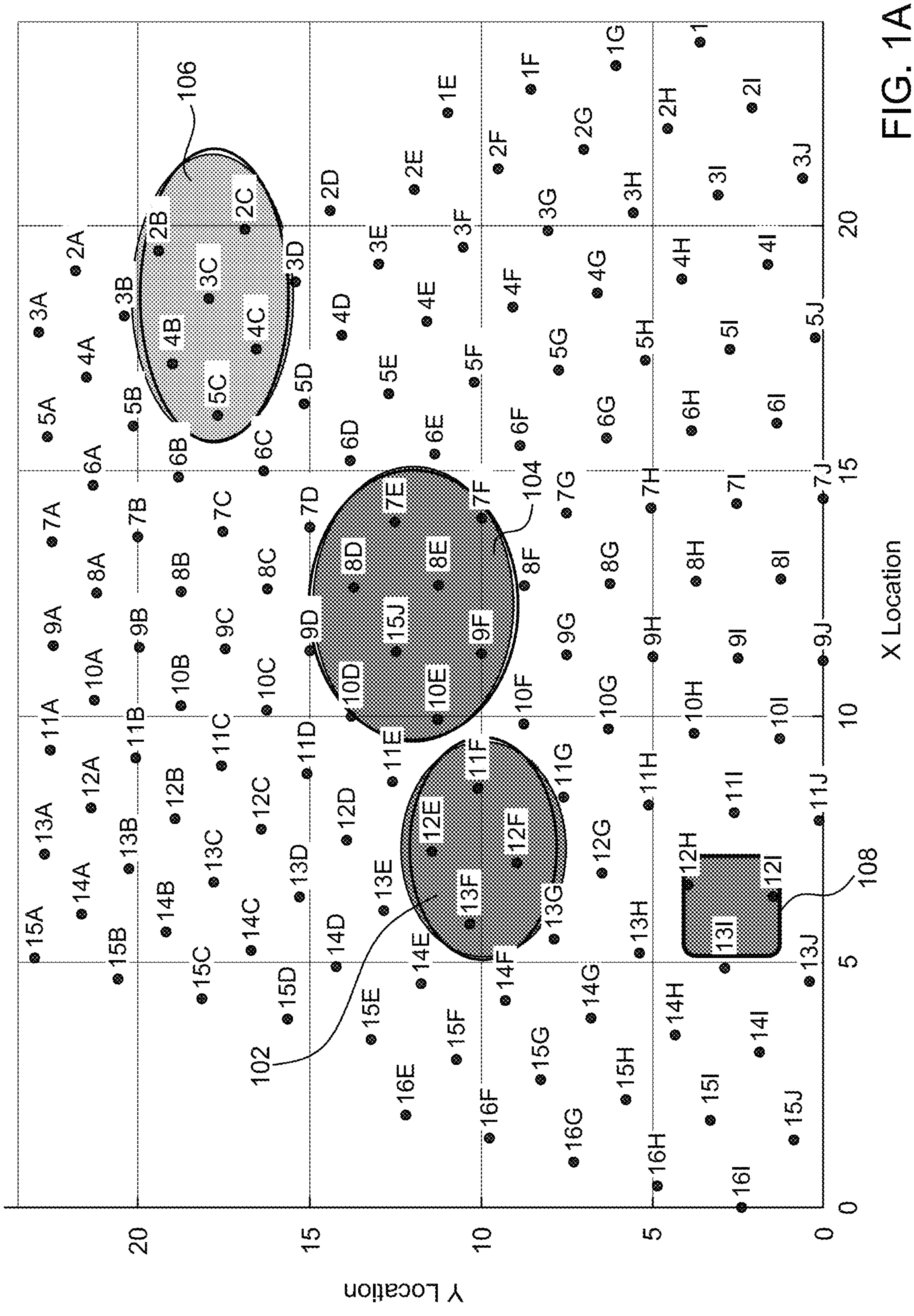
FIGS. 1A and 1B illustrate a first example of NMES calibration in accordance with this disclosure.

The NMES calibration system and device disclosed in this disclosure may be a computing device, such as be a computer, a laptop, a smartphone, or any other device which may perform data receiving and data processing as described in this disclosure. The computing device may comprise a variety of hardware, such as processor, memory and any other components necessary for running software/algorithm to process data. Since those components of the computing device are well-known, here in this disclosure, a detailed description of those components will be omitted. There may be a slight difference between the definition of system and the definition of device. For example, the system may comprise more peripheral components than the device. However, in this disclosure, unless otherwise indicated, the terms "NMES calibration system" and "NMES calibration device" may be used interchangeably.

In an embodiment, the NMES calibration device may be a component of a complex NMES system. For example, the NMES system may comprise the NMES calibration device and a NMES sleeve. In that case, the NMES calibration device may be used to improve calibration of the NMES sleeve.

In another embodiment, the NMES calibration device may be a device independent of a complex NMES system. For example, the NMES calibration device may receive data/signal from the NMES system (e.g., from sensors within the NMES system), process the data and improve calibration of the NMES system.

In an embodiment, the NMES system disclosed in this disclosure may be a NMES garment (or any wearable) which may be attached to a user for treatment. For example, the NMES device may be a NMES sleeve, NMES band, NMES shirt, or NMES pants. The NMES system may also be an implanted system.

It should be noted that the above examples of the NMES device are not intended to be exclusive or be limiting to the present disclosure. Any other electrical stimulation devices may be used as long as they are accordance with the principles taught or disclosed in this disclosure. In this disclosure, unless otherwise indicated, the terms "NMES system" and "NMES device" may be used interchangeably.

In an embodiment, the NMES system may also be used in a massage garment wherein the garment spatially translates the ROIs to provide a massage to the user.

It should be appreciated that the NMES system disclosed in this disclosure may be a complex which may comprise one or more of the above-mentioned NMES devices. For example, a NMES system may comprise both a NMES sleeve and NMES band. In that scenario, a user may use the NMES sleeve and the NMES band for treatment at the same time. A NMES system may also comprise a variety of different components, such as cameras, sensors, processors, etc. Those components may be already well-known on the market and thus a detail description of them may be omitted from this disclosure.

It should be appreciated that although the relationship between the NMES calibration device and the NMES device has been described, that description is not intended to be exclusive or be limiting to the present disclosure. Any available relationship between the NMES calibration device and the NMES device may be applicable as long as they are in accordance with the principles of this disclosure. For example, the NMES calibration device may be a cloud computing device or a distributed system.

Figure 1B:
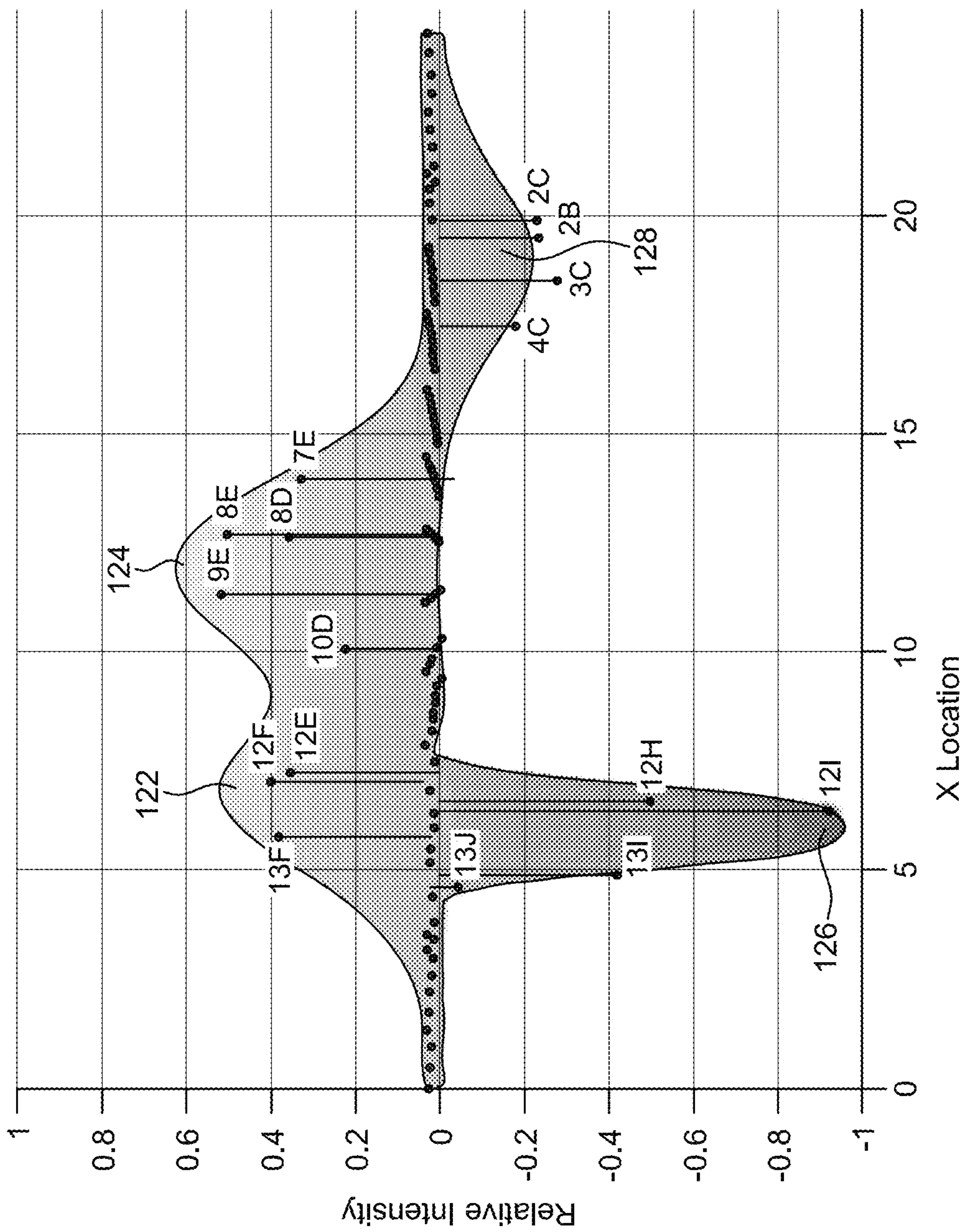
Figure 2A:
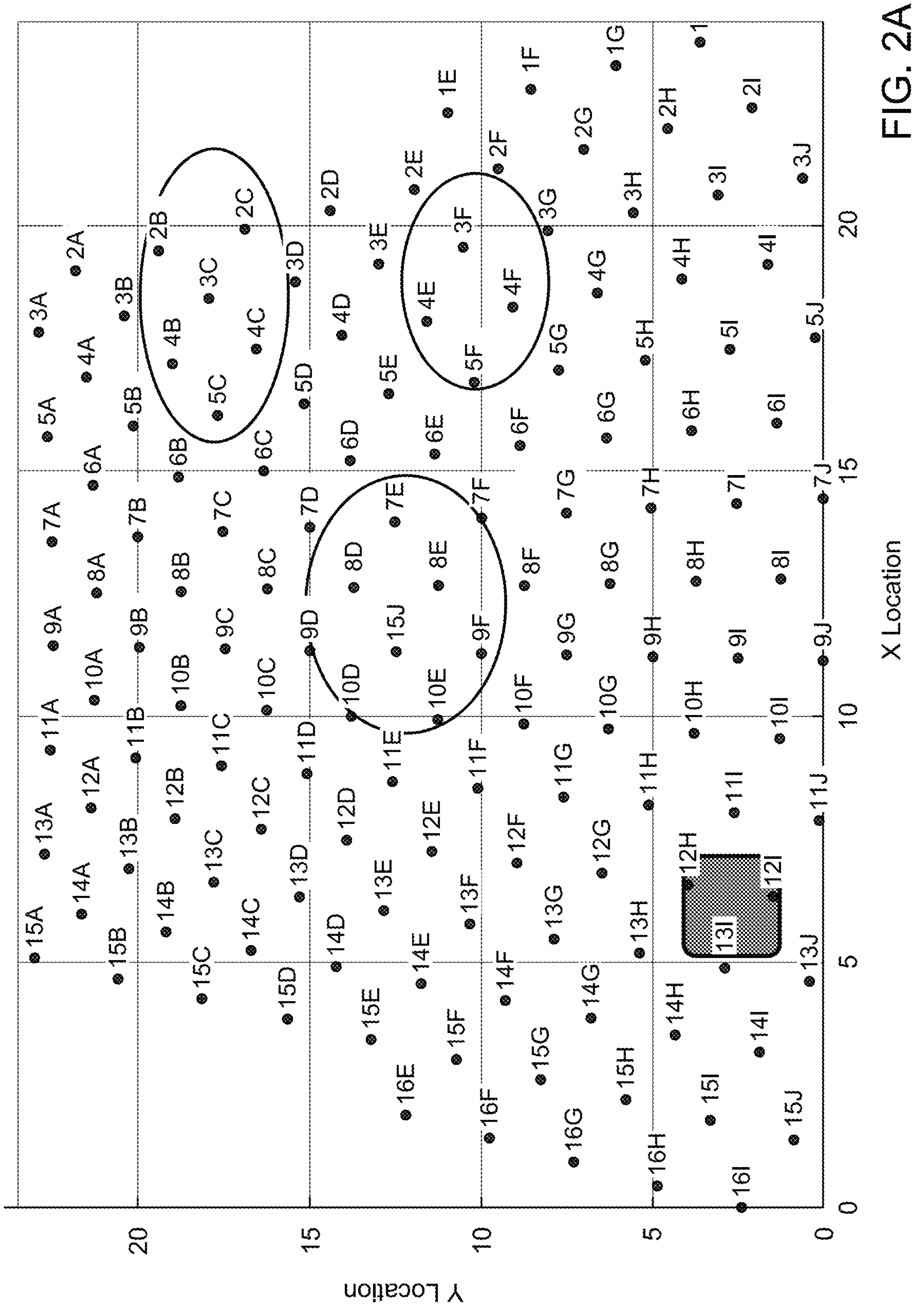
FIGS. 2A and 2B illustrate a second example of NMES calibration in accordance with this disclosure.
Figure 2B:
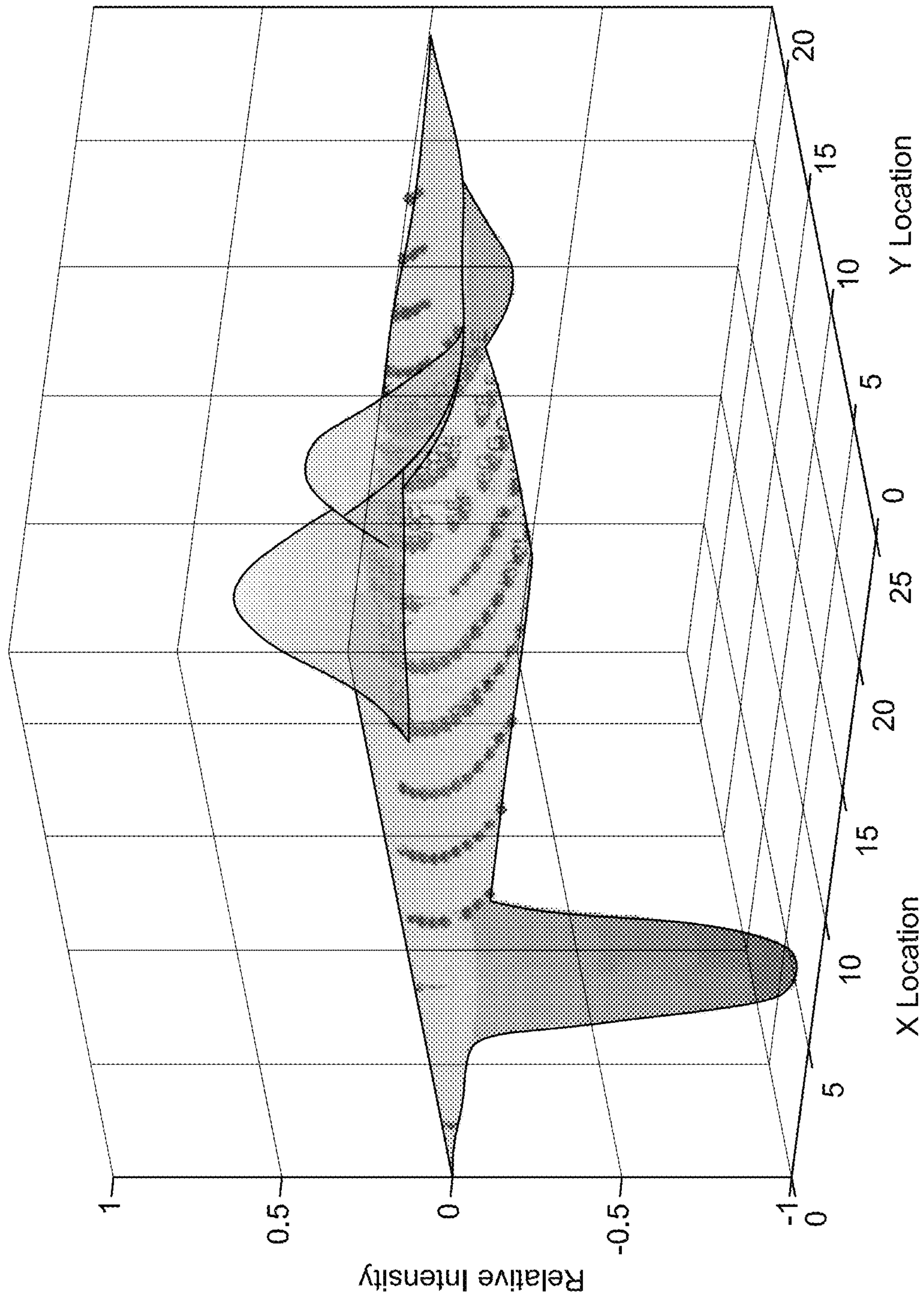

The NMES calibration device and the NMES calibration method in accordance with this disclosure will be described below with reference to FIGS. 1A-2B. FIGS. 1A and 1B illustrate a first example of NMES calibration in accordance with this disclosure. FIGS. 2A and 2B illustrate a second example of NMES calibration in accordance with this disclosure. The NMES calibration method will be described below with reference to FIGS. 1A-2B and FIG. 3. The NMES calibration method may be performed by the above-discussed NMES calibration device.

Figure 3:
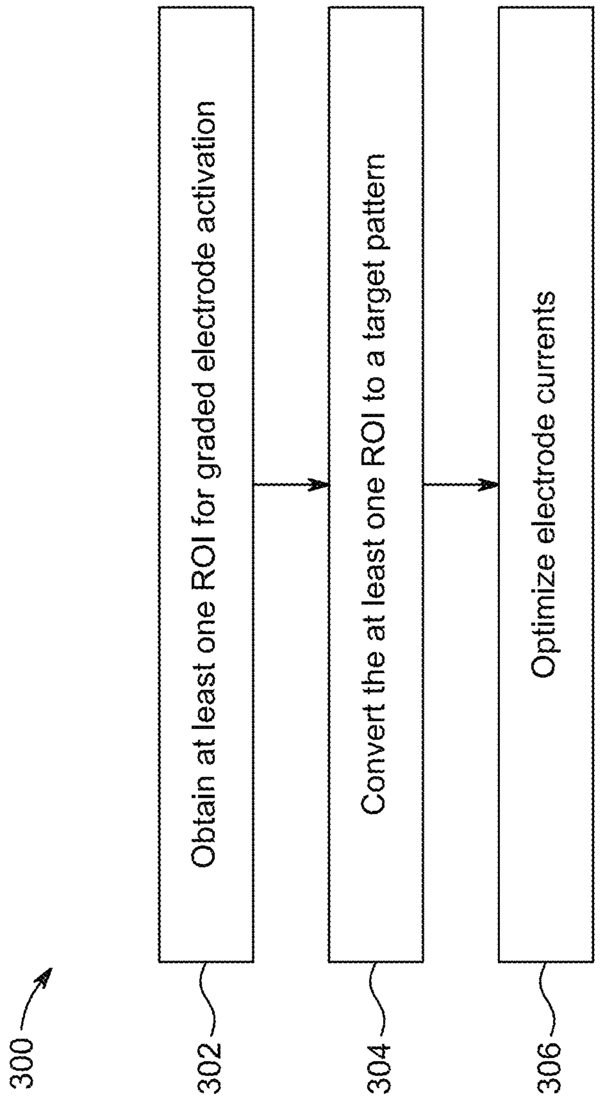
FIG. 3 is a flowchart of a method of NMES calibration in accordance with this disclosure.

As shown in FIG. 3, the method may comprise the following processes from 302 to 306: at 302, obtaining at least one region of interest (ROI) for graded electrode activation; at 304, converting the at least one ROI to a target pattern; and at 106, optimizing electrode currents. The processes will be described in detail below.

At 302, a ROI for graded electrode activation may be defined. For example, an operator and/or user may define a ROI for graded electrode activation. The ROI may be translated and scaled in real time during NMES. In an example, the operator may define a ROI before a user uses the NMES device. In another example, the operator may define a ROI while a user is using the NMES device. In an embodiment, one ROI or multiple ROIs may also be defined. In this disclosure, unless otherwise indicated, the terms "ROI" and "ROIs" may be used interchangeably.

Figure 4:
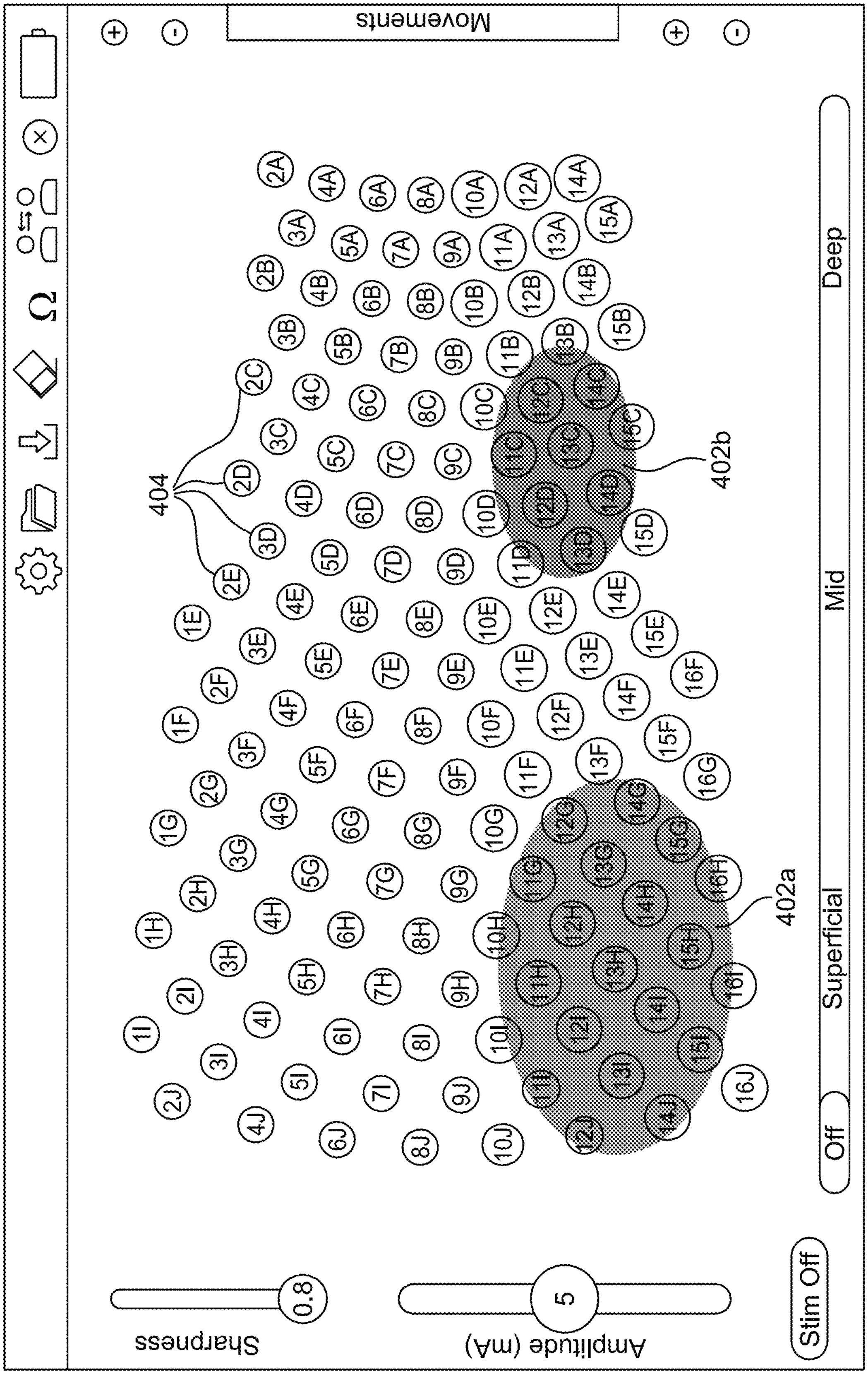
FIGS. 4 to 8 illustrate an exemplary GUI in accordance with this disclosure.
Figure 5:
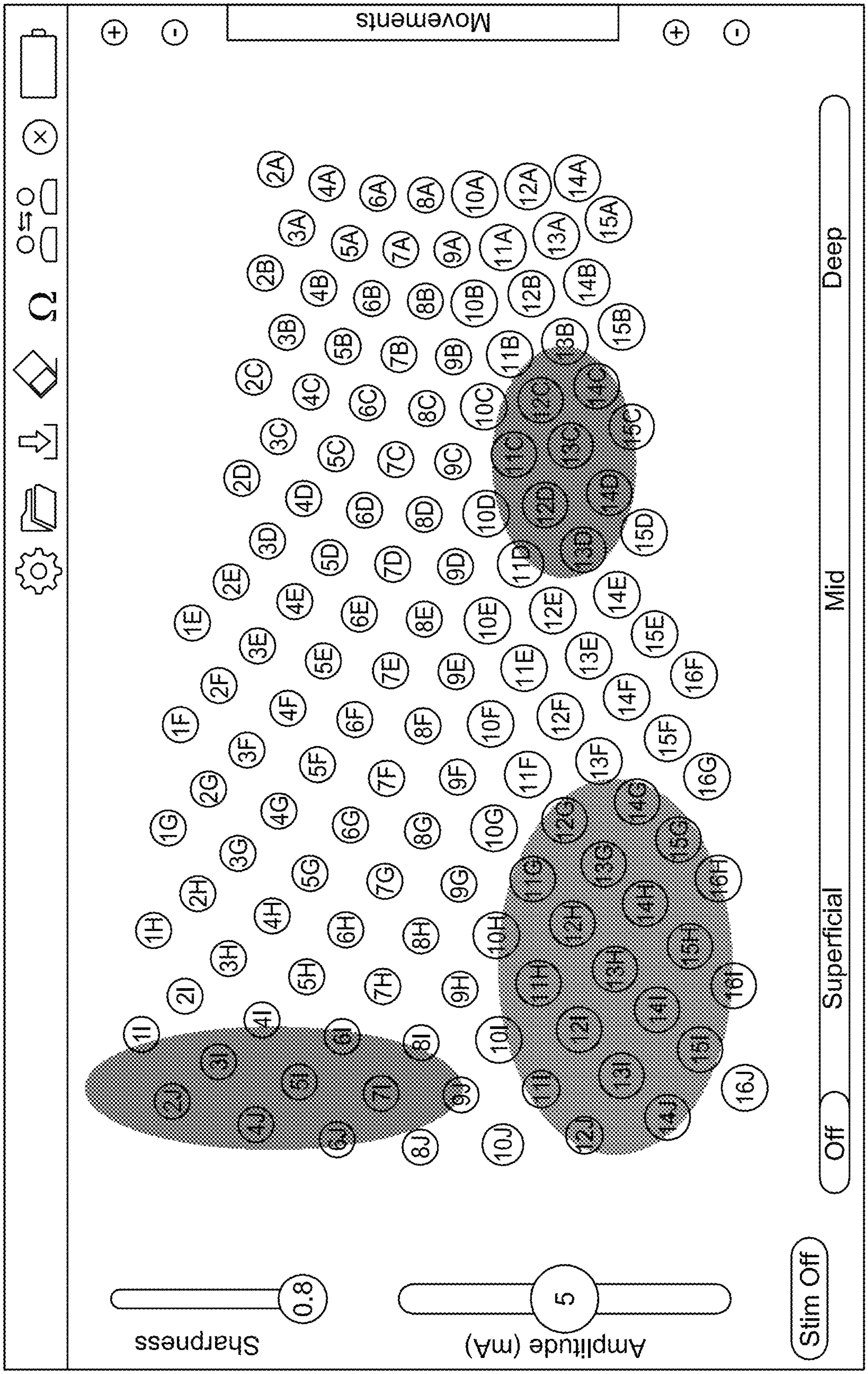

As shown in FIG. 4 and FIG. 5, the ROI may be defined through a graphic interface. The graphic interface may be provided by the NMES calibration device. For example, the NMES calibration device may comprise a monitor and a graphic interface is provided and shown on the monitor. The operator may select a two-dimensional region 402*a* and 402*b* on the graphic interface and further drag and/or resize the region to ultimately define a ROI. The graphic interface may be implemented as a NMES electrode mapping which represents a mapping of virtual electrodes 404 shown on the graphic interface to physical electrodes in the NMES system.

Figure 6:
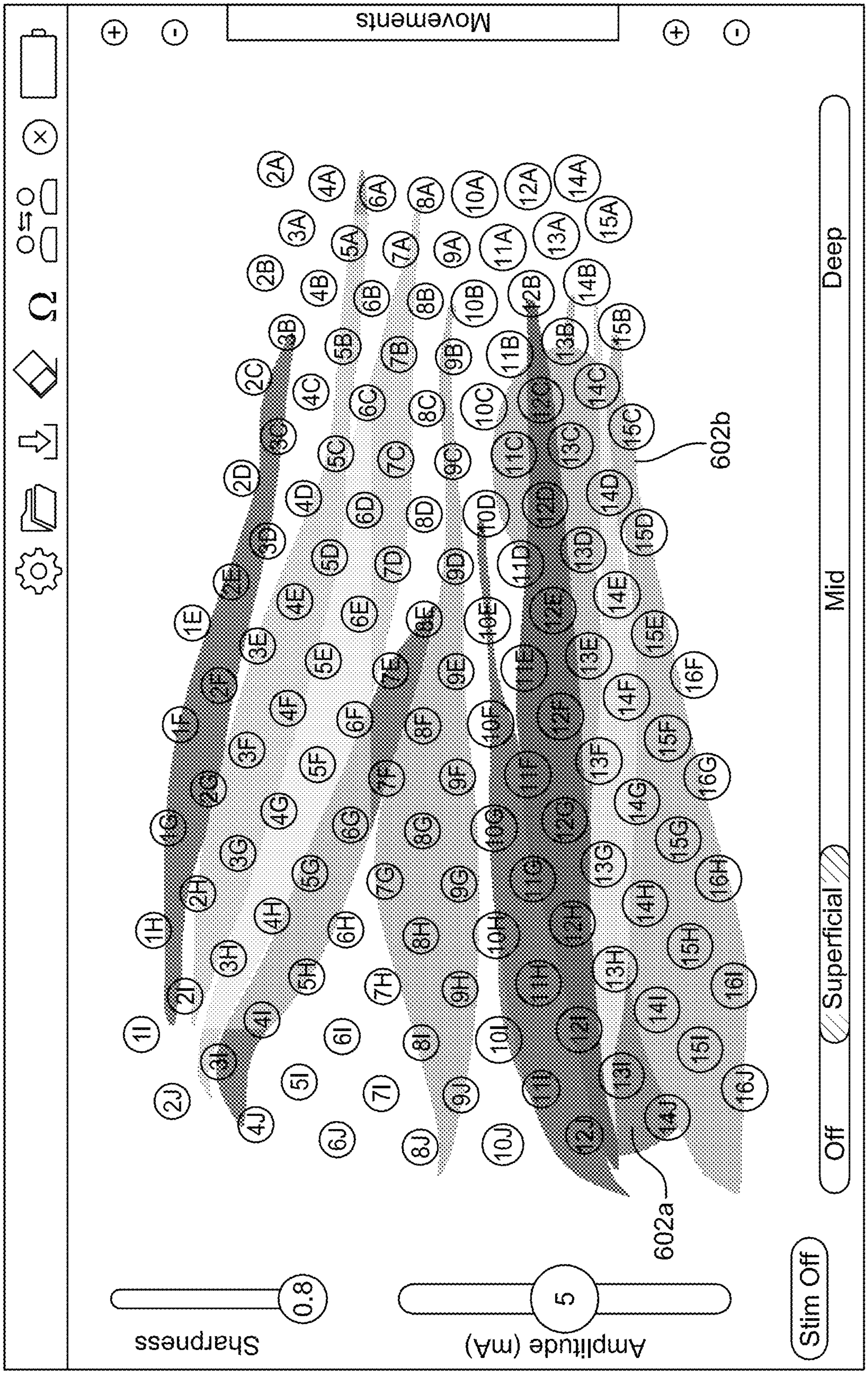
Figure 7:
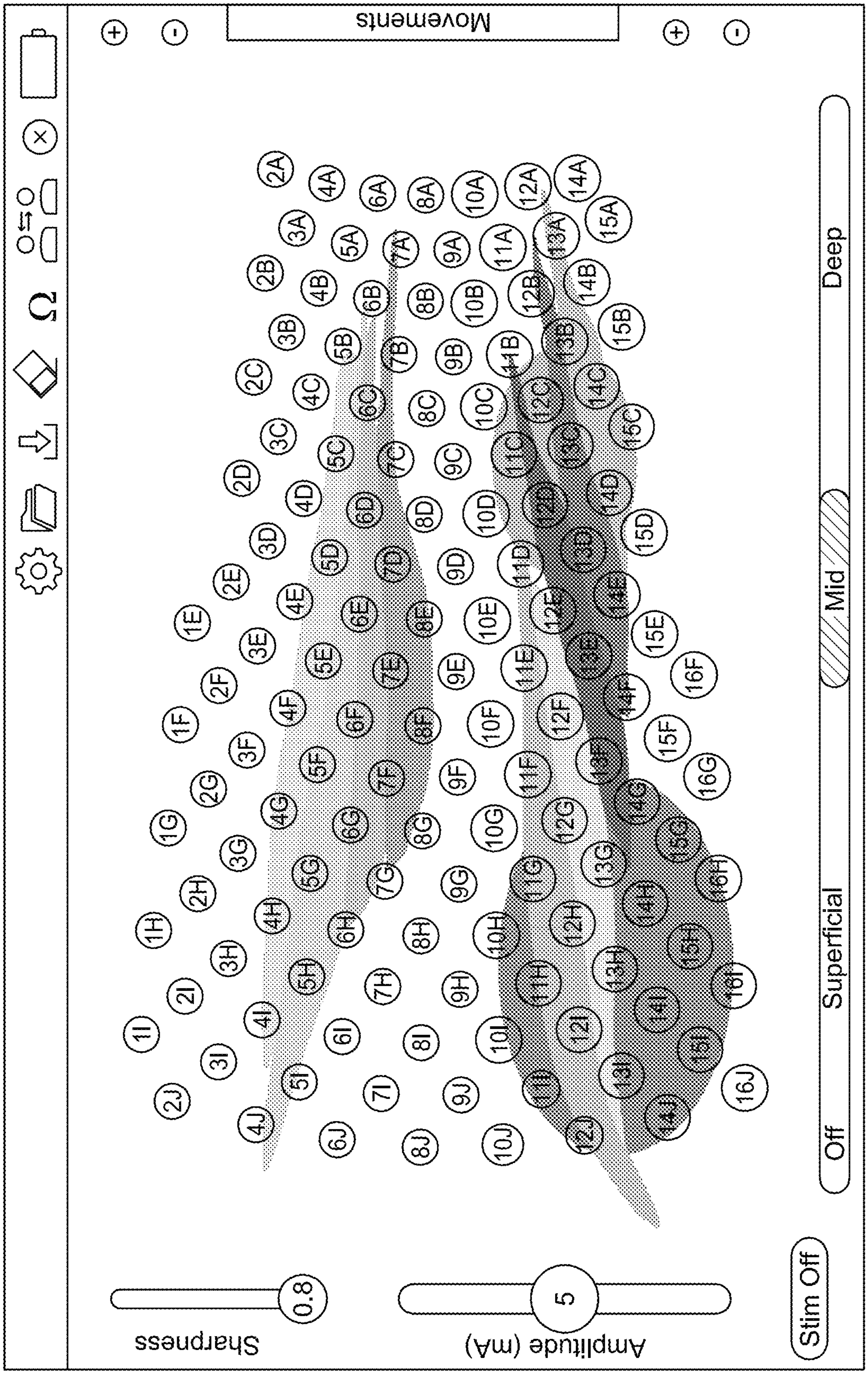
Figure 8:
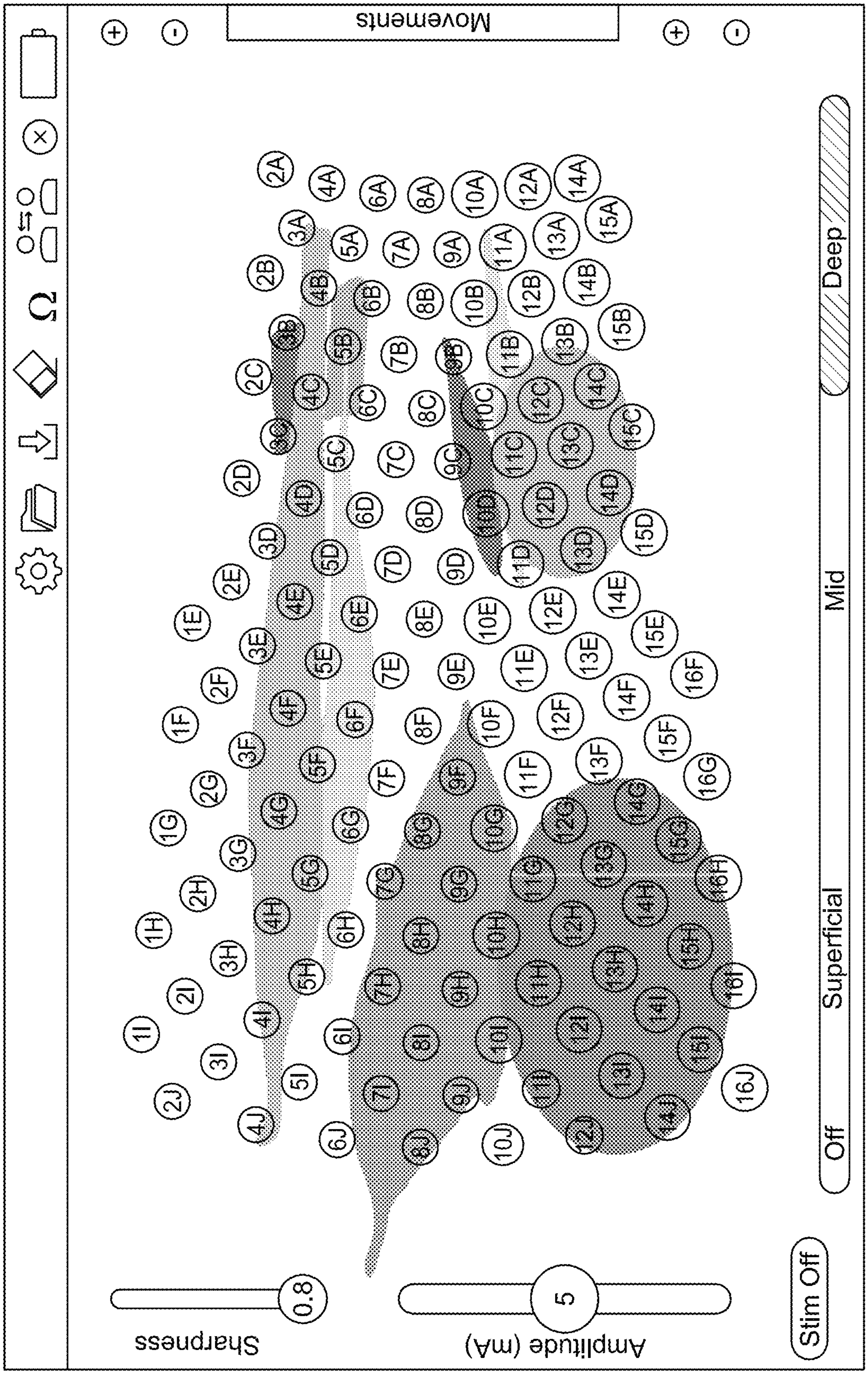

As shown in FIG. 6 to FIG. 8, the ROI can also be defined to target specific areas of a muscle. As shown in FIG. 6, ROIs 602*a* and 602*b* may target a specific portion of the muscle. This may allow the operator to perform specific movements for the user. For example, the operator can define the ROI to target the specific muscles responsible for raising an arm or closing a fist.

As shown in FIGS. 1A and 2A, the X-Y coordinate system may represent a graphic interface with a NMES electrode mapping. The NMES electrode mapping may indicate a relationship between the electrodes in the NMES device (not shown) and the corresponding virtual electrodes shown on the graphic interface (e.g., 8D and 9E shown in FIG. 1A). As shown in FIG. 1A, there are four ROIs, 102, 104, 106, and 108, defined by the operator. The four ROIs 102, 104, 106, and 108 are shown in circles and rectangle.

In an embodiment, the operator may manually define ROIs through the graphic interface. For example, the operator may define ROI 108 at the bottom of FIG. 1A and identify it by a rectangle, and then may define a ROI 104 in the middle of FIG. 1A and identify it by a circle. It should be noted that the above example of defining ROIs is not intended to be exclusive, and the ROIs may be defined in different sequences.

After a ROI has been defined, the operator may also drag, move or resize the defined ROI. For example, if a user is wearing a NMES sleeve, the operator may define an ROI as the start of the session. However, as the user moves his or her arm, an alignment inconsistency may occur. In this scenario, the operator may drag the ROI to a new position to get proper alignment. Further, the operator may resize the ROI.

In another embodiment, a ROI may be defined without any operator's actions. For example, a ROI may be predefined before an operator uses the NMES system. In that scenario, the NMES calibration device may be pre-configured with a ROI configuration, and once an operator begins to use the NMES system, a ROI will be defined based on the pre-configured ROI configuration.

A ROI may also be defined by the NMES calibration device based on its detection of a user's movements. For example, the NMES may use sensors to detect the user's movements, and then transmit the collected data to the NMES calibration device. The collected data may then be processed by the NMES calibration device and a determination regarding ROI may also be generated by the NMES calibration device. A ROI may be defined based on the determination. This process of defining the ROI may be performed repeatedly in real time. Therefore, the NMES calibration device may define a new ROI once it detects the user's movements. In an embodiment, once a new ROI is defined, the previous ROI may be removed.

ROIs may be defined by any continuous or discrete function over two dimensional spatial locations. In one embodiment an ROI may be defined by the following equation (hereinafter "Equation 1"):

$$M(x, y; s, c, t) = \frac{s}{\left(1+e^{c*(-x+t_{x1})}\right)\left(1+e^{c*(x+t_{x2})}\right)\left(1+e^{c*(-y+t_{y1})}\right)\left(1+e^{c*(y+t_{y1})}\right)}$$

$$t = (t_{x1}, t_{x2}, t_{y1}, t_{y2})$$

where M(x, y; s, c t) calculates the electrical current for the electrode at position x, y with ROI parameters s, c, t. In this equation, parameter s defines whether the electrode is set to a cathode or anode and this parameter can take the values of s={−1, 1}. Parameter c represents the ROI "steepness", or how quickly the stimulation intensity increases relative to neighboring electrodes. Parameter t is a vector specifying the upper and lower location bounds of the ROI in the x and y direction. Parameters s, c, and t are set when the ROI is defined as described previously. A combination of these ROIs produces an output like that shown in FIG. 1B and FIG. 2B.

In another embodiment, an ROI may be defined by the following equation (hereinafter "Equation 2"):

$$M(x, y; s, a, \sigma, t) = \frac{s * a}{\pi\sigma^4} * \left(1 - \left(\frac{(x - t_x)^2 + (y - t_y)^2}{2\sigma^2}\right)\right) * e^{-\frac{(x-t_x)^2+(y-t_y)^2}{2\sigma^2}}$$

$$t = (t_x, t_y)$$

where M(x, y; s, a, σ, t) calculates the electrical current for the electrode at position x, y with ROI parameters s, a, σ, t. In this equation, parameter s defines whether the ROI peak is a cathode or anode and this parameter takes the values of s={−1, 1}. Parameter a represents the ROI amplitude. Parameter σ modifies the shape of the ROI. Parameter t is a vector specifying the location of ROI in the x and y direction. Parameters s, a, σ and t are set when the ROI is defined as described previously. Based on Equations 1 and 2, it should be apparent that any function over the two-dimensional spatial locations can be used to define an ROI. It should be noted that above exemplary functions are only given by way of example, and it's not intended to be exclusive. Any other function may be available as long as it may help to realize the principles disclosed in this disclosure. For example, a gaussian function may also be used to convert the ROI to a target pattern. In this case, the ROI may be defined in the same or similar manner as discussed above, but in some scenario, underlying parameters used to define the ROI may be different from those above. For example, the width of the ROI may define the width or standard deviation of the gaussian.

It should be noted that when a ROI is defined, it can be recognized by the NMES calibration device using software or algorithm. It should be appreciated that the above-discussed equations may be implemented by using software or algorithm.

In an embodiment, the method 300 may further comprise scanning the defined ROI across the NMES device to identify functional movements. The functional movements may be multi-planar and/or multi-joint movements. For example, the functional movements may comprise any one or combination of squat, lunge, hinge, push, pull, and carry motions. Therefore, after scanning the defined ROI across the NMES device, the NMES calibration device may identify functional movements from the user. The NMES calibration device may use the identified functional movements to update the ROI, define a new ROI, and/or improve NMES calibration. The updated ROI may also be defined/obtained through the above equations.

In an embodiment, there may be a software or an algorithm pre-configured in the NMES calibration device, and thus, the NMES calibration device may use the software/algorithm to process the sensor data from the NMES system, determine and define ROIs.

In an embodiment, ROIs may be defined based on muscle geometry of a user. That is, different muscle geometry may be directed to different ROIs. In an embodiment, the operator may define ROIs based on different parameters of muscle geometry. The parameters of muscle geometry may comprise muscle strength, muscle lines, 3D muscle shape, etc. For example, if a user of the NMES sleeve has a strong muscle on their arm, the operator may define ROIs differently than what they may do for a user who has a weak muscle on their arm. It should be noted that the above-discussed muscle strength is only one of multiple parameters of the muscle geometry. ROIs may also be defined based on other parameters, such as 3D muscle shape.

In another embodiment, ROIs may be defined based on a user-specific anatomical feature. The user-specific anatomical feature may comprise at least one of the following sub-features: joint position, joint length, bone length, etc. For example, if the operator wants to improve NMES calibration for muscles around a user's wrist, he may define, through the above-discussed graphic interface, ROIs corresponding to the user's wrist. In other words, he may define ROIs including electrodes corresponding to the muscles around the user's wrist.

Figure 9A:
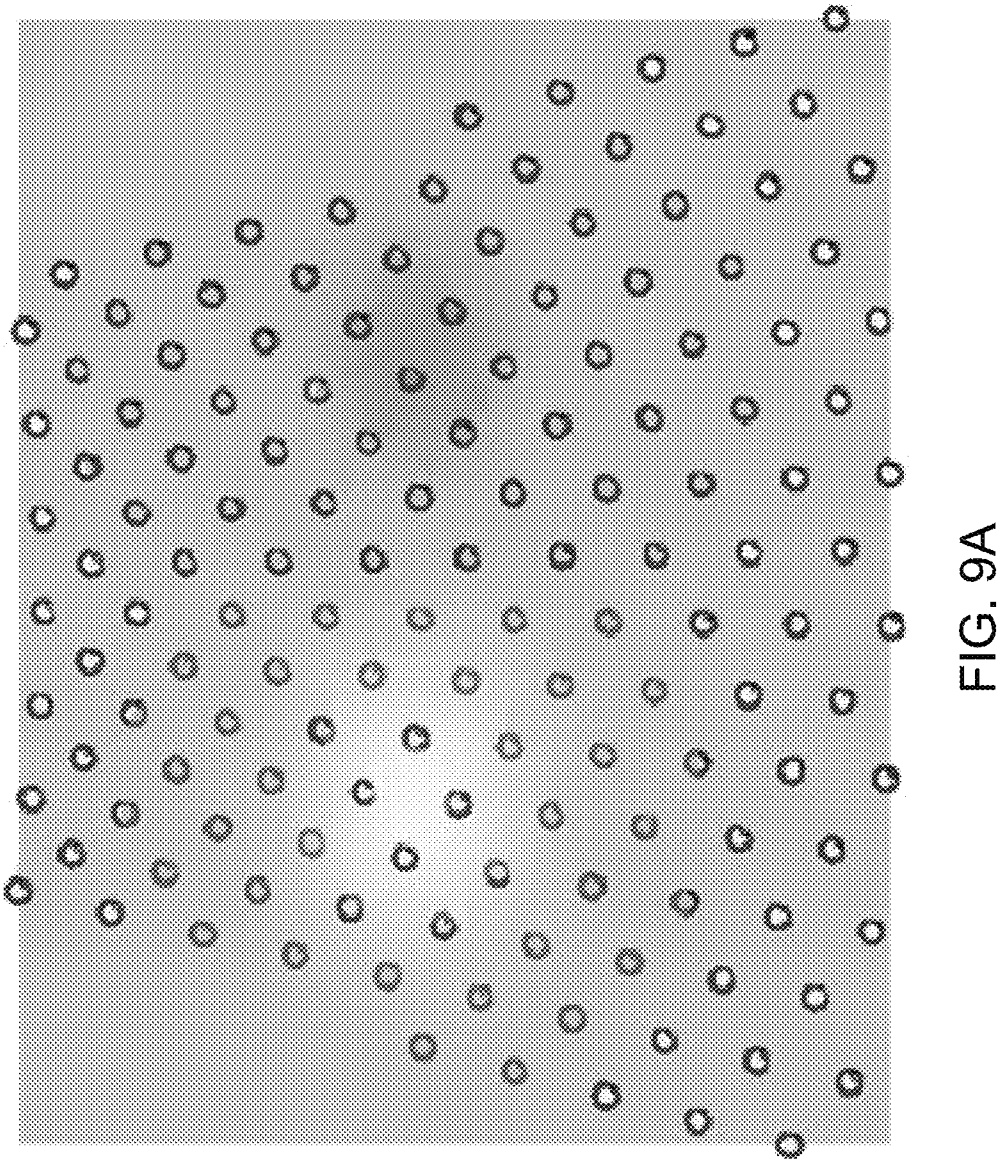
FIGS. 9*a* to 11*b* illustrate exemplary ROIs as defined via the GUI.
Figure 9B:
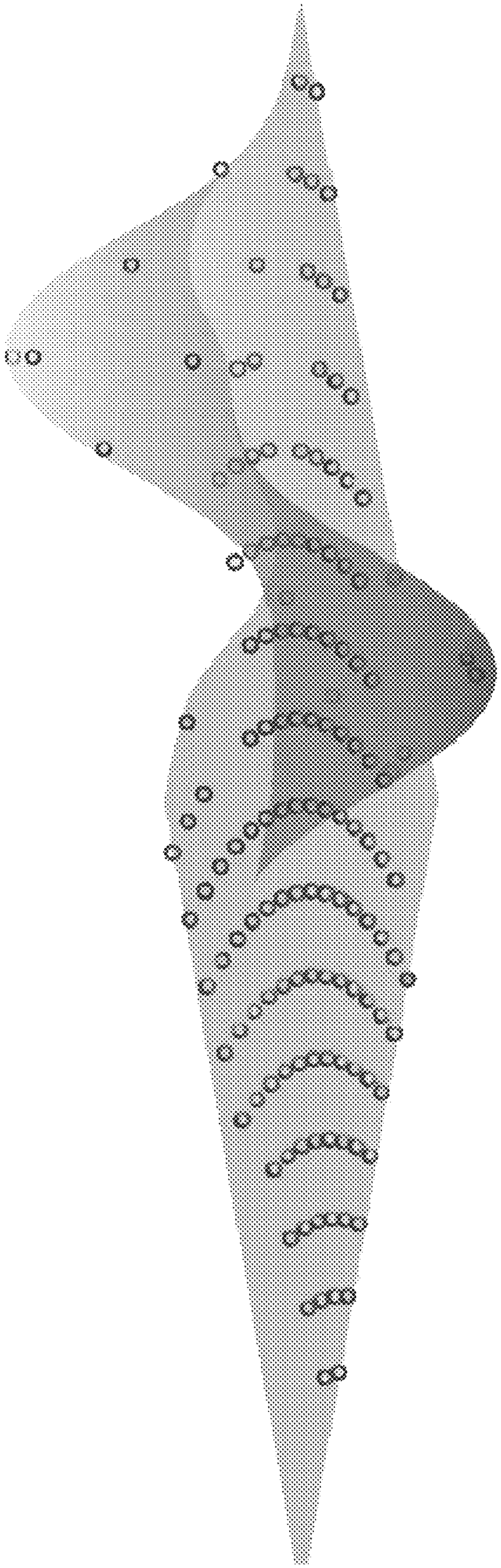
Figure 10A:
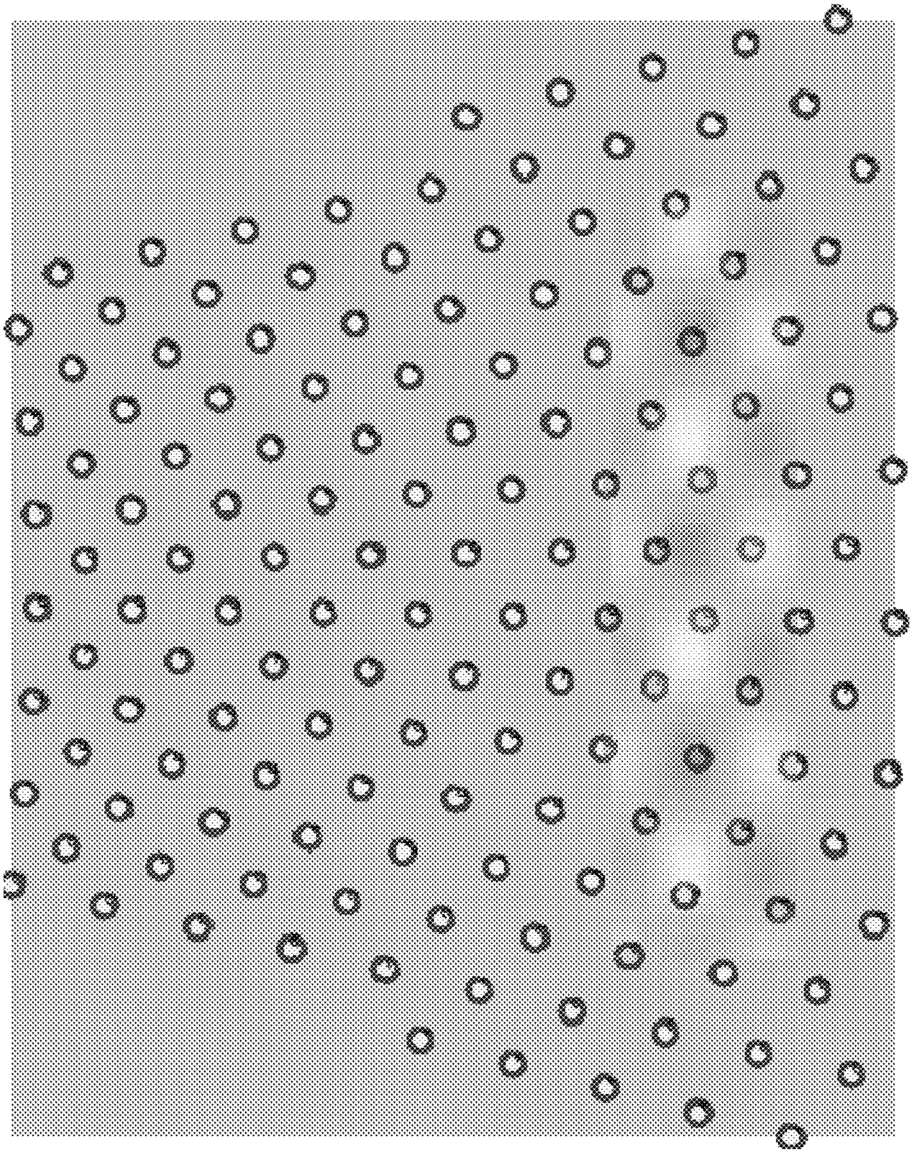
Figure 10B:
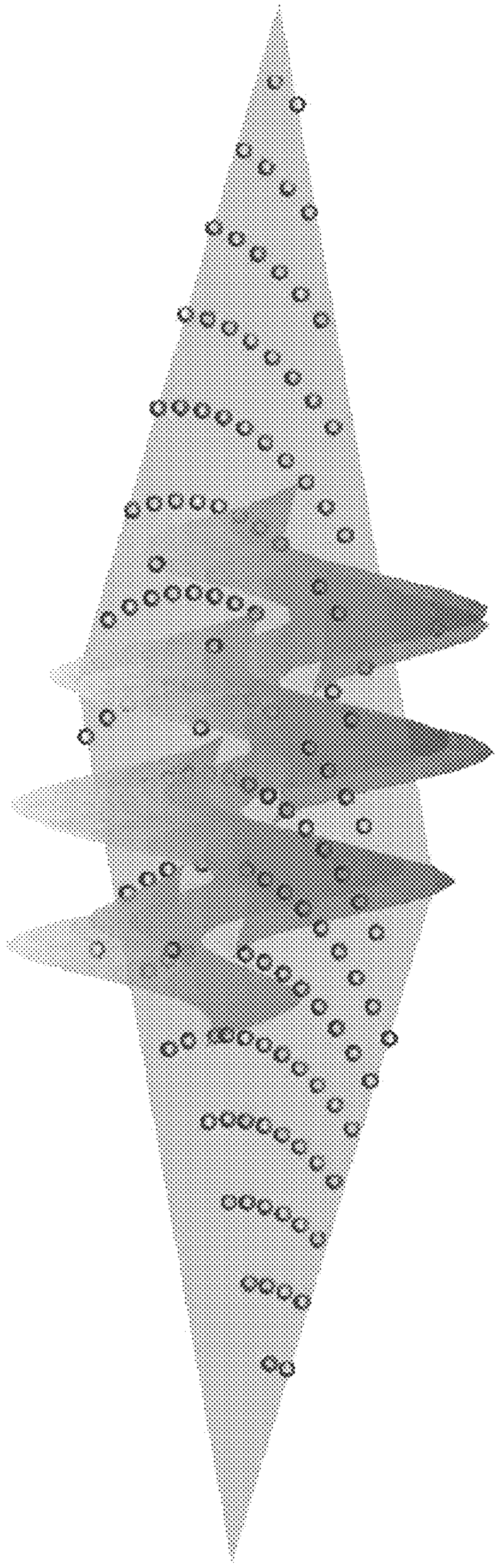
Figure 11A:
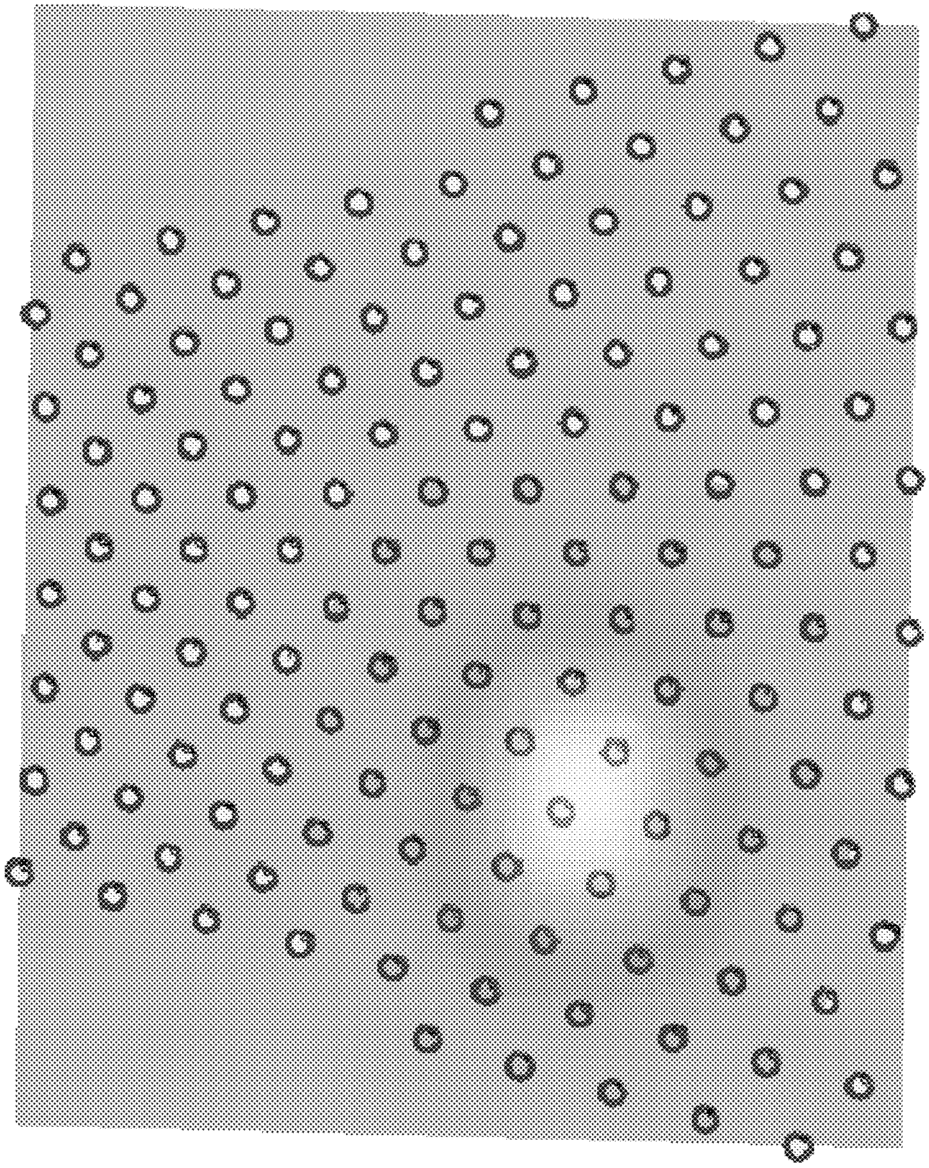
Figure 11B:
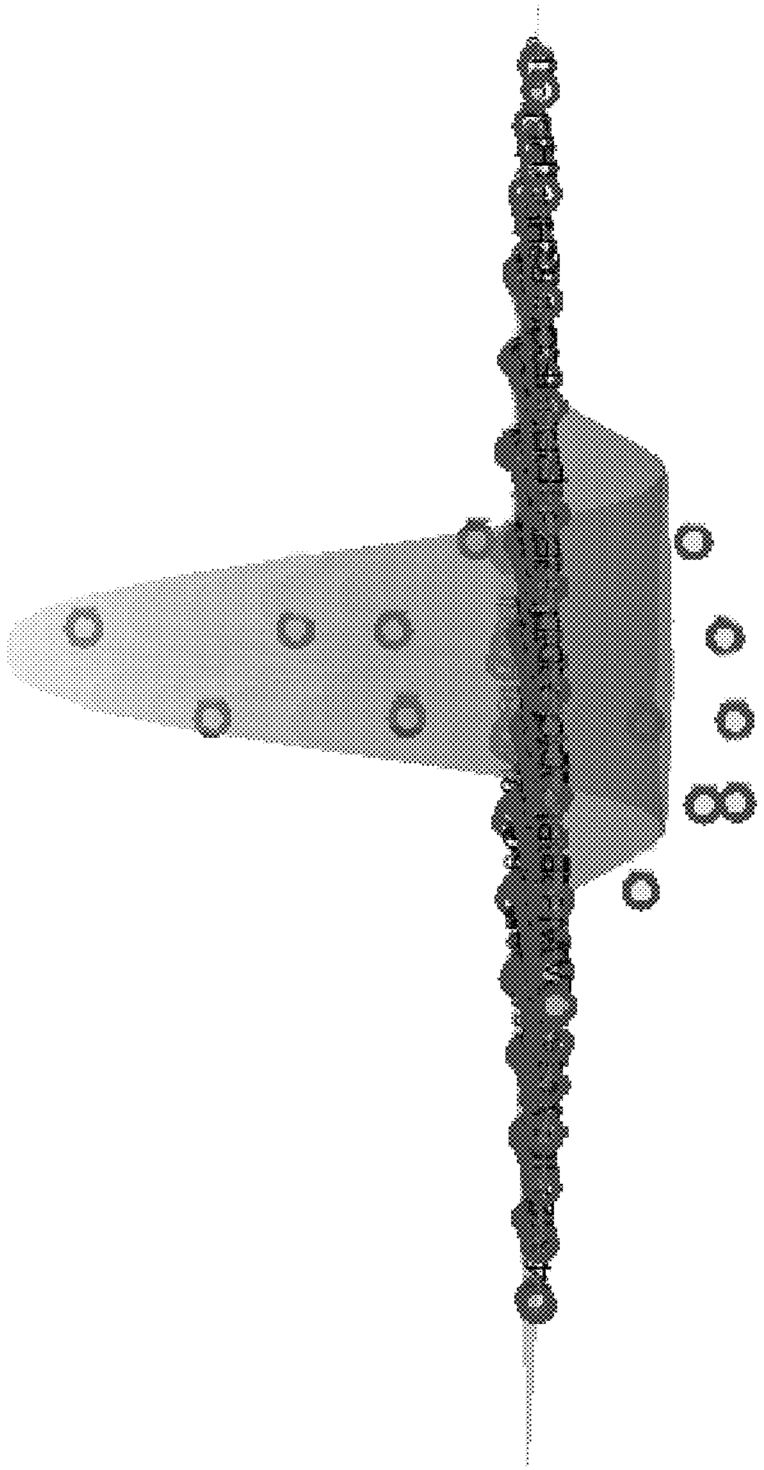

It should be noted that the above examples regarding how to define ROIs are not intended to be exclusive or be limiting to the present disclosure, and the ROI may be defined through any other available ways as long as they are accordance with the principle of this disclosure. Additional ROIs are shown in FIGS. 9*a* to 11*b*. As shown in FIG. 9*a*, it is possible to have just one single ROI that includes both a cathodic and anodic region.

In an embodiment, in order to generate a target pattern, the combination of all ROIs must contain at least one cathodic region and at least one anodic region for NMES. In other words, the operator may select at least one cathodic ROI and at least one anodic ROI, or they may select one ROI with both cathodic and anodic regions for NMES. For example, as shown in FIG. 1A, four different ROIs have been selected and two of them are cathodic ROIs (ROI 106 and ROI 108) and the other two are anodic ROIs (ROI 102 and ROI 104). It should be appreciated that the examples shown by FIGS. 1A and 2A do not intended to be exclusive or be limiting to the selection of ROIs. For example, an operator may select one cathodic ROI and two anodic ROIs.

In another embodiment, the operator may also define a relative intensity of a ROI. The relative amplitude can be used to modify the electrical stimulation intensity after generating the target pattern and optimizing electrode current values (described below).

At 304, the ROI defined at 302 may be converted to a target pattern. In an embodiment, the target pattern is a 2-dimensional pattern (e.g., shown in FIG. 1B). In another embodiment, the target pattern is a 3-dimensional pattern (e.g., shown in FIG. 2B). It should be noted that the 2-dimension pattern shown in FIG. 1B does not intended to be exclusive or be limiting to the present application. For example, a 3-dimensional pattern may be generated in the scenario shown in FIG. 1A, and the computing device may further show that 3-dimensional pattern on a monitor by just viewing the figure down the y location axis, so that a corresponding 2-dimensional pattern may be shown on the monitor. In an embodiment, if the ROI only has a 1-dimension of electrodes (e.g., a strip/line of electrodes), then a corresponding target pattern may be two dimensional.

In an embodiment, the NMES calibration device may convert the ROI to a 3-dimensional target pattern (as shown in FIG. 2B) using the following equation (hereinafter, "Equation 3"):

$$Z(x,y;\theta_n)=\Sigma_n M(x,y;\theta_n)$$

where n is equal to the number of ROIs and $\theta_n$ is the set of parameters defining the nth ROI. The target pattern can be comprised of different types of ROIs. For instance, one ROI may be generated by Equation 1 and a second ROI by Equation 2 (these are the functions M(x,y) demonstrated earlier) and they may be combined using Equation 3.

It should be noted that Equation 3 above is only given by way of example and it not intended to be exclusive. Equation 3 is only one possible way in which various ROIs can be added together to generate a target pattern. For example, a weighted combination is also possible.

The target pattern may be provided by the NMES calibration device and shown on its monitor. As shown in FIG. 1B, the upward peeks 122 and 124 correspond to the ROIs 102 and 104 shown in FIG. 1A; the downward peak 126 corresponds to the ROI 108 shown in FIG. 1A; the downward peak 128 correspond to the ROI 106 shown in FIG. 1A. The target pattern may be used for NMES calibration which will be described below later. FIGS. 2A and 2B are similar to FIGS. 1A and 1B except that in FIGS. 2A and 2B, ROI 102 and upward peak 122 have been translated across the garment.

At 306, the electrode currents may be optimized. In an embodiment, electrode currents may be imposed to the ROI. That is, the NMES system may impose electrode currents to those electrodes within the ROI. The electrode currents may be optimized real time by minimizing the mean squared error between the target pattern and actual electrode currents while linearly or non-linearly constrained by safe stimulation parameters and NMES hardware limitations. Also, other types of objective functions may be used to optimize the electrode currents. As shown in FIG. 1B, the target pattern may be used to optimize the electrode currents. That is, to minimize the mean squared error between the target pattern and actual electrode currents, an optimized electrode current value of an electrode within the ROI may have to be closed to the outline of the target pattern.

To minimize the error between current electrode currents and the target pattern while maintaining safe stimulation parameters may be implemented using the following equation (hereinafter "Equation 4"):

$$L = \sum_{q \in E_{x,y}} (q - Z(x, y))^2$$

Equation 4 evaluates the total difference between the optimized current values of electrodes $E_{x,y}$ at positions x,y and the target ROI at the respective x,y positions. However, the system is not limited to the function L as described above. For example, any function that quantifies the difference between optimized electrode current values and the target ROI may be used. For example, the function may be defined as (hereinafter "Equation 5"):

$$L = \sum_{q \in E_{x,y}} |q - Z(x, y)|$$

The optimized electrode current values $E_{x,y}$ are found by minimizing L while abiding by n number of G constraints: $G \in \{G_1, G_2, \ldots G_n\}$.

$$G_1(E)=\Sigma_{q\in E_{x,y}} q=0 \quad \text{(Equation 6) (Net neutral charge)}$$

$$G_2(E)=|\{e\in E_{x,y}:e>0\}|\leq 10 \quad \text{(Equation 7) (Limit \# (+) electrodes)}$$

$$G_3(E)=|\{e\in E_{x,y}:e<0\}|\leq 10 \quad \text{(Equation 8) (Limit \# (−) electrodes)}$$

$$G_4(E)=E_{x,y}\in E_{Disabled}=0 \quad \text{(Equation 9) (Disabled electrodes=0)}$$

$$G_5(E)=E_{x,y}\in E_{User}=V_{x,y} \quad \text{(Equation 10) (Enforce electrodes value)}$$

The above functions (Equations 6-10) may not be used to calculate the electrode values, but instead they may provide limits on the range of solutions of optimization. For example, they may force an electrode value to be 0 (disabled), or require that the sum of electrode currents for both cathodic and anodic electrodes be 0. While an algorithm may minimize the function L (i.e., Equation 5), it may not select values $E_{(x,y)}$ that are outside of these ranges.

It should be noted that the above equations are not intended to be exclusive, and they may change for different NMES systems/devices. Constraints may be imposed by safe stimulation parameters, by hardware limitations, by user preferences, or through any other means. For example, Equations 7 and 8 may limit the number of positive and negative electrodes to 10 each if a NMES system has a max number of 10 cathodic and 10 anodic electrodes at any given time. This could be more, less, or a non-existent constraint for other NMES systems. Similarly, Equations 9 and 10 are optional ways to enforce electrode values.

For example, as shown in FIG. 1B, an optimized electrode current value of the electrode 13F is close to the outline of the target pattern. As shown in FIG. 1B, an optimized electrode current value of the electrode 8E is close to the outline of the target pattern. It should be noted that in these figures, dots with labels correspond to an optimized electrode current value of a NMES electrode. Therefore, the NMES calibration device may obtain optimized electrode current values (i.e., graded electrode currents) respectively corresponding to those electrodes within the ROI, and then it may output the optimized electrode current values to the NMES device and the NMES device will impose the optimized electrode currents to those electrodes in the ROI. Therefore, the NMES calibration is improved.

It should be noted that because of constrains including net neutral charge and a maximum number of simultaneously active electrodes, some electrodes may deviate from the target pattern. For example, as shown in FIG. 1B, the electrode 3C deviates from the target pattern.

An interior-point algorithm may be used to optimize the electrode current values in the current implementation. Other solvers tailored for minimizing a constrained multivariable function are possible.

Real time optimization of electrode currents may ensure smooth, graded electrode currents while operating within safe stimulation parameters. This may allow for continuous transitions between target movements.

Correlations between ROIs across time and between subjects can be used as input to the above-mentioned algorithm that autonomously adjusts for variability in electrode placement or anatomical differences.

Because the NMES calibration method may provide calibration faster than 10× per second, the operator may adjust the ROIs in real time while delivering electrical stimulation, and immediately observe the movement outcomes. This NMES calibration method 300 may accelerate NMES calibration by allowing the operator to make quick and precise electrode adjustments.

Correlation analysis, machine learning algorithms, and other statistical approaches may be able to leverage relationships between ROIs and evoked movements to track and compensate for variabilities in electrode placement. For instance, a transfer function that aligns the peaks of a target pattern for a single movement from the prior session may be applied to previously calibrated grips to compensate for electrode shifts.

Therefore, it can be seen that the NMES calibration systems, devices and methods disclosed in this disclosure may improve system recalibration through ROIs (e.g., high-resolution ROIs) that can be adjusted in real-time, thereby eliminating the repetitive trial and error procedure due to manual calibration. In addition, the ROIs may be correlated across time to detect variabilities in electrode placement, conferring additional benefits over discrete electrode activations.

In some NMES systems, the cathodes may be placed over the target muscle while anodes are placed away from the cathodes, for example, in areas that do not simulate muscles (e.g., wrist or joints).

One stimulation system is a bipolar stimulation system, where current flows from a cathode to an anode. In a bipolar stimulation system, the current density under both the cathode and the anode can cause muscle activation.

Figure 12:
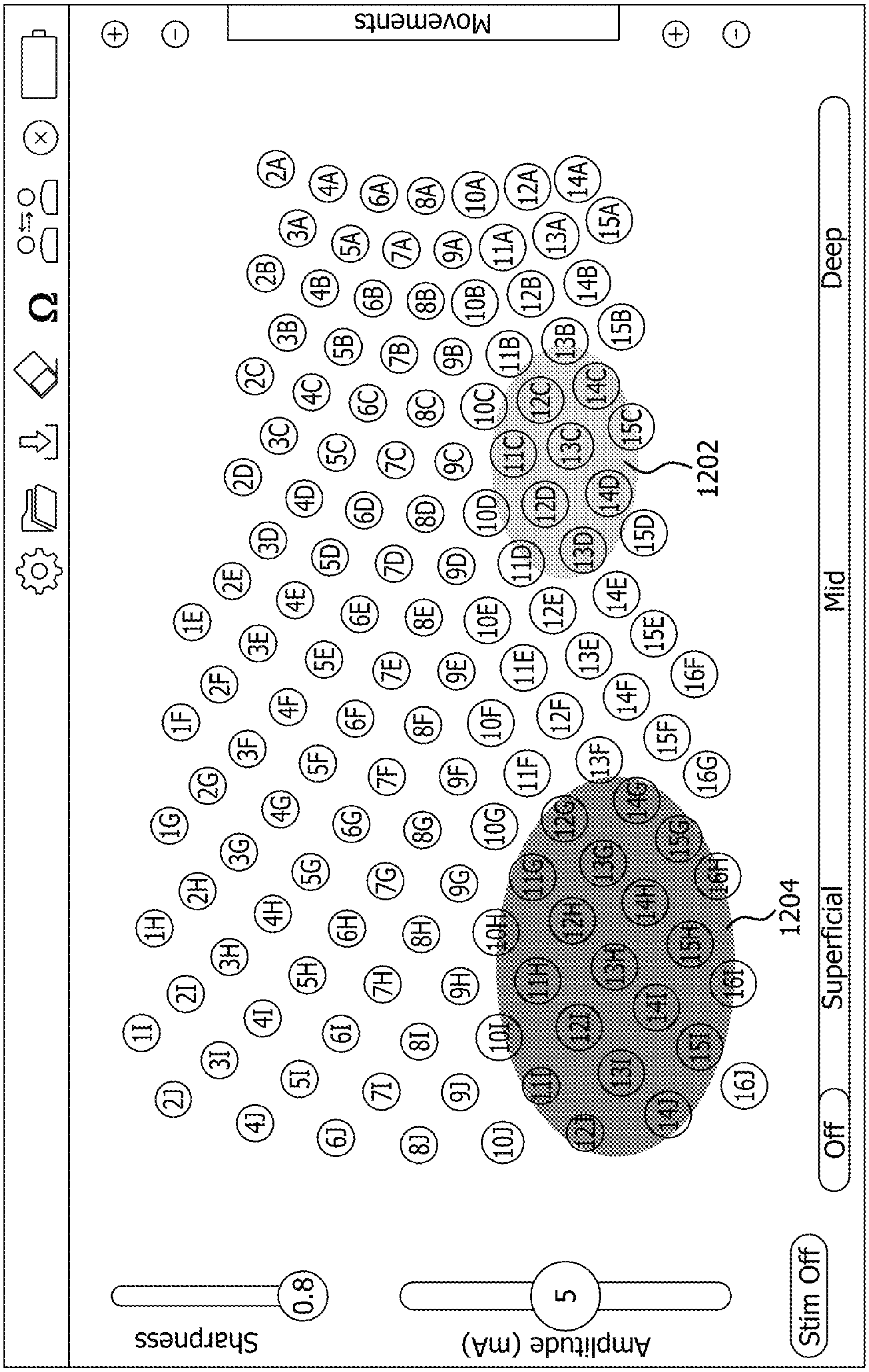
FIG. 12 illustrates a bipolar stimulation system.

FIG. 12 illustrates a bipolar stimulation system. Region 1202 represents the cathodes and region 1204 represents the anodes. As shown, the anode region 1204 is located away from the cathode region 1202.

One problem with a bipolar system is that the patch of anodes still provide some level of stimulation, which can be painful to the user in certain circumstances. For example, in a high-density electrode sleeve (as described above), the cathode group of electrodes may be placed over a target muscle, while the anode group of electrodes may be placed at a location away from the cathode region in an area where muscle simulation is not desired. However, because of the high density of anodes in that region, some muscle simulation may still occur. This can lead to undesired results along with pain to the user.

To minimize the issue of unwanted muscle stimulation by anodes, a pseudomonopolar stimulation system may be used for muscle stimulation. As discussed above, the disclosed system allows an operator to select which of the plurality of electrodes to designate as a cathode and which of the plurality of electrodes to designate as an anode. This provides flexibility to the operator on where and how to place the cathodes and anodes.

Figure 13:
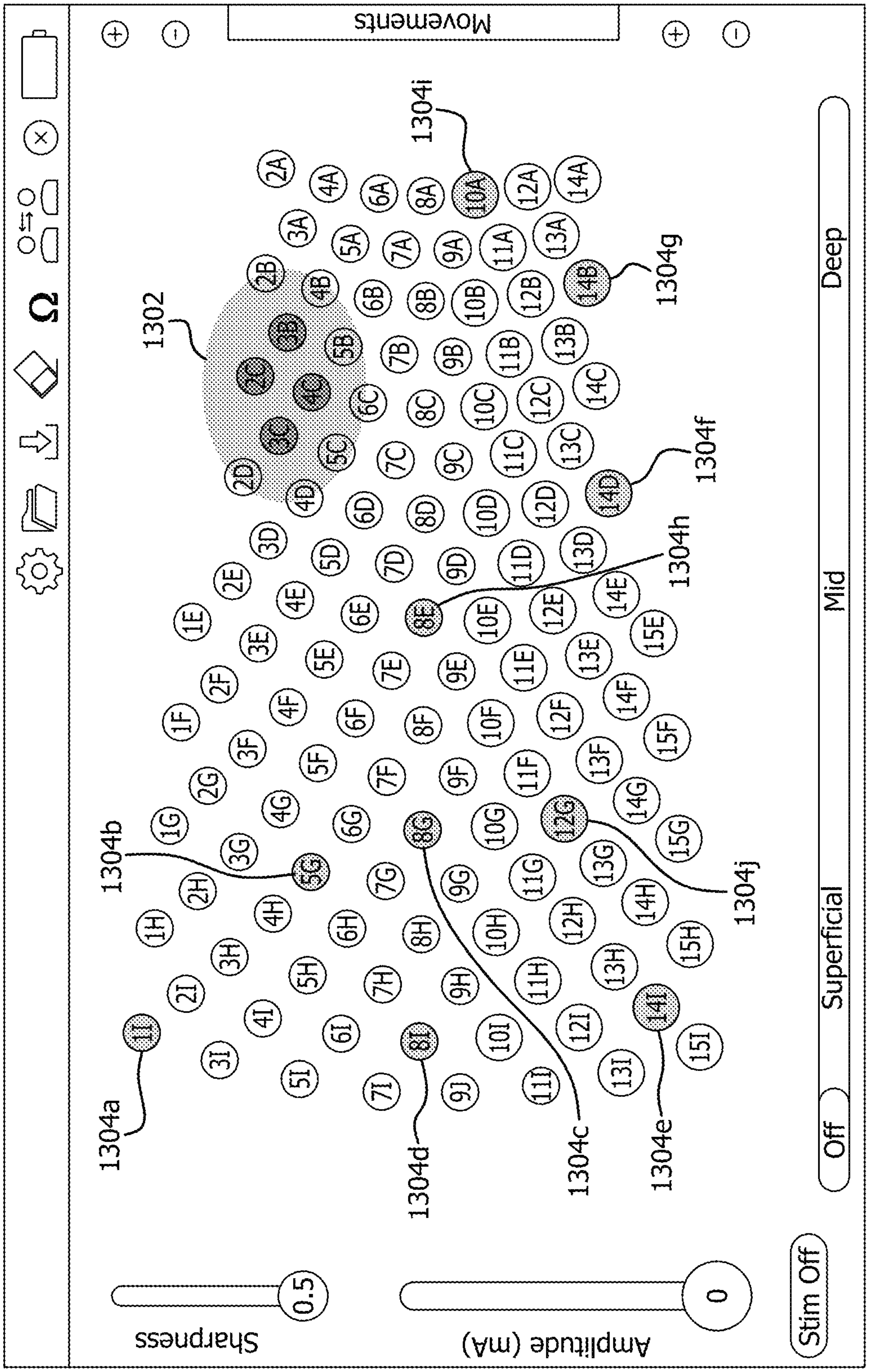
FIG. 13 illustrates a pseudomonopolar stimulation system.

FIG. 13 illustrates a pseudomonopolar stimulation system. In pseudomonopolar stimulation system, after the operator and or system determines the group of electrodes to designate as the cathodes, the system disperses the anodes among the other electrodes. The operator may designate region 1302 as a cathode region. As seen in FIG. 13, anodes 1304*a*-1304*j* are dispersed among the rest of the inactive electrodes. Because the anodes are dispersed, the current is distributed across a larger area, which results in a lower current density, and thus, lower muscle activation.

After the operator has placed the cathode regions, the system may use various methods to determine the placements of the anodes among the inactivated electrodes. All inactivated electrodes may be assigned as anodes, or a subset of these inactivated electrodes may be selected algorithmically to minimize the current density near the anodes, such as through optimization or heuristic.

In one example, anodes are initially placed at a random subset of inactivated electrodes. Anode placement is then optimized using an iterative method that repositions anodes closest to active electrodes and places them at the furthest inactive electrode position from active electrodes. This process is repeated until the average distance of anodes relative to other active electrodes stops increasing.

In another method, the system may use equidistributed sequences to determine the best location for each of the anodes. For each anode, the location may be assigned to the inactive electrode closest to the next point in a equidistributed sequence. If the location is within a threshold distance from another active electrode, the anode is reassigned to an inactive electrode closest to the next point in the sequence. Because equidistributed sequences approximate a uniform distribution in the space, the chosen anode locations will be far from any other anode.

In one example, the distributed electrodes, including active cathodes and anodes, have an equally balanced current. In another example, the distributed electrodes have non-uniform current amplitudes. In another example, the anodes may be limited to a specific region.

A pseudomonopolar stimulation may also operate in the reverse polarity where an operator places anode regions and the placements of cathodes are dispersed among inactivated electrodes. Operating in the reverse polarity can improve targeted muscle activation depending on stimulation waveform parameters.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random-access memory (RAM), a register, cache memory, semiconductor memory devices, magnetic media such as internal hard disks and removable disks, magneto-optical media, and optical media such as CD-ROM disks, and digital versatile disks (DVDs).

It will be appreciated that the terminology used in the present application is for the purpose of describing particular embodiments and is not intended to limit the application. The singular forms "a", "the", and "the" may be intended to comprise a plurality of elements. The terms "including" and "comprising" are intended to include a non-exclusive inclusion. Although the present application is described in detail with reference to the foregoing embodiments, it will be appreciated that those foregoing embodiments may be modified, and such modifications do not deviate from the scope of the present application.

What is claimed is:

1. A system for electrical stimulation, comprising:

a plurality of electrodes; and a processor;

wherein the processor is configured to:

define a region of interest (ROI) for electrode activation via a first subset of the plurality of electrodes, the first subset including active electrodes and the electrodes of the plurality not included in the first subset comprising inactive electrodes;

define a second subset of electrodes of the plurality of electrodes, the second subset comprising anodes selected from the inactive electrodes by:

(i) initializing the second subset by selecting anodes at a random subset of the inactive electrodes;

(ii) iteratively repositioning anodes closest to the active electrodes to inactive electrode positions farthest from the active electrodes; and (iii) terminating the repositioning when an average distance between the anodes and the active electrodes stops increasing.

2. The system of claim 1, wherein the first subset of electrodes are cathodes.

3. The system of claim 1, wherein the anodes are limited to a specific region.

4. The system of claim 1, wherein the processor is further configured to provide electric muscle simulation via the subset of the plurality of electrodes.

5. The system of claim 1, wherein the second subset of electrodes are defined via low-discrepancy sequences.

6. The system of claim 1, wherein the second subset of electrodes are defined via an equidistributed sequence.

7. The system of claim 1, wherein the first subset of electrodes and second subset of electrodes have an equally balanced current.

8. The system of claim 1, wherein the plurality of electrodes are part of a wearable garment.

9. The system of claim 1, wherein the plurality of electrodes are part of an implantable device.

10. The system of claim 1, wherein the system for electrical stimulation is for muscle stimulation.

11. The system of claim 1, wherein the plurality of electrodes are placed in proximity to a muscle to be stimulated.

12. The system of claim 1, wherein the system for electrical stimulation is for electrical neural stimulation.

13. The system of claim 1, wherein the plurality of electrodes are placed in proximity to a nerve to be stimulated.

* * * * *